United States Patent [19]

Jarque et al.

[11] 4,174,396
[45] Nov. 13, 1979

[54] 7,10-DIMETHYL-5,9-IMINO-4,5,8,9-TETRAHYDRO-CYCLOOCT[b]THIOPHENES AND A PROCESS FOR OBTAINING IT

[75] Inventors: Ricardo Grandados Jarque, Barcelona; Mercedes Alvarez Domingo, San Juan Despi; Juan Bosch Cartes, Barcelona; Cirstobal Martinez Roldan; Fernando Rabadan Peinado, both of Madrid, all of Spain

[73] Assignee: Laboratories Made, S.A., Madrid, Spain

[21] Appl. No.: 892,599

[22] Filed: Apr. 3, 1978

[51] Int. Cl.² .................. C07D 513/18; A61K 31/44
[52] U.S. Cl. ......................... 424/256; 546/80
[58] Field of Search .............. 260/294.8 B; 424/256; 256/80

[56] References Cited
U.S. PATENT DOCUMENTS 3,626,068 12/1971 Suh ............................ 546/80
3,681,351 8/1972 Wellings ....................... 546/80
3,704,237 11/1972 Suh ............................ 546/80
3,767,659 10/1973 Suh ............................ 546/80

Primary Examiner—Alan L. Rotman
Attorney, Agent, or Firm—Ladas, Parry, Von Gehr, Goldsmith & Deschamps

[57] ABSTRACT

Compounds of the formula:

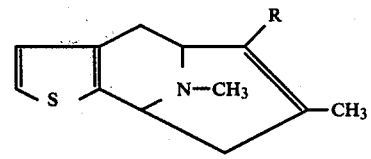

where R is H or lower alkyl and a process for the preparation thereof are disclosed. The compounds are analgesic agents.

5 Claims, No Drawings

7,10-DIMETHYL-5,9-IMINO-4,5,8,9-TETRAHYDRO-CYCLOOCT[b]THIOPHENES AND A PROCESS FOR OBTAINING IT

This invention relates to obtaining 7,10-dimethyl5,9-imino-4,5,8,9-tetrahydro-cyclooct[b]thiophenes of formula I, in which R can be H (I,R=H) or an alkyl group, for example methyl (I,R=CH₃), and the addition salts thereof with pharmacologically acceptable acids, for example picrates as well as analgesic compositions containing same. The mentioned compounds are new substances of possible interest as analgesics, and are prepared according to the following reaction sequence:

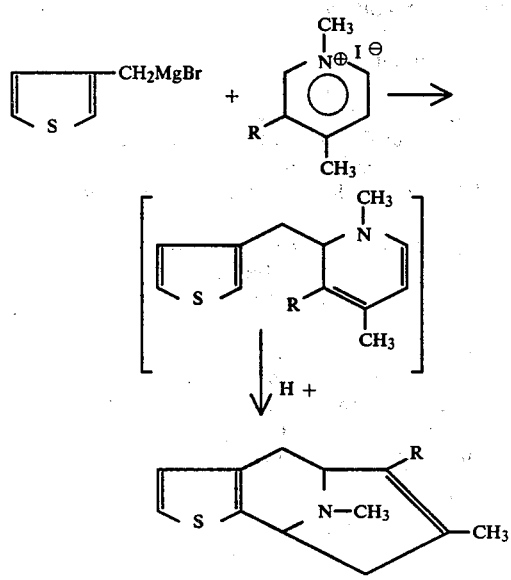

In the first step of the process, 3-thenylmagnesium bromide is obtained in conditions of high dilution and in inert atmosphere and is made to react at reflux temperature with a N-methylpyridinium iodide in anhydrous ether, an unstable dihydropyridine intermediate being obtained which without subsequent purification is treated in acid medium. After alkalinization of the resulting solution and extraction with an organic solvent the corresponding 7,10-dimethyl-5,9-imino-4,5,8,9-tetrahydro-cyclooct [b]thiophene (I) is obtained, and is purified and characterized in picrate form.

The following examples are given merely as illustrations and must not be considered in any way limitative of the scope of the invention.

EXAMPLE 1

Obtaining 7,10-dimethyl-5,9-imino-4,5,8,9-tetrahydrocyclooct[b]-thiophene (I,R=H)

To obtain the 3-thienylmagnesium bromide, use has been made of the "modified cyclic reactor" containing a continuous flow column provided with a separation funnel, coolant and reaction flask. The reactor column is packed with 70 g of magnesium shavings alternated with thin layers of mercuric chloride, and is covered with a saturated solution of mercuric chloride in anhydrous ether. Following 12 hours of standing, 250 ml of anhydrous ether are introduced in a flask and refluxed for two hours. The flask is replaced by another equipped for mechanical stirring in which 10 g of 1,4-dimethylpyridium iodide are introduced in 150 cc of anhydrous ether. 8 g of 3-thenyl bromide are placed in the separation funnel in 75 ml of anhydrous ether. A few ml of the halogenide solution are added to the meganesium column, and when it is observed that the reaction has begun the flask is heated to reflux temperature, the addition continuing slowly for two hours. Nitrogen atmosphere is maintained in the system during the entire process. When addition has concluded, reflux is continued for one hour and 30 minutes. The ether solution is poured over 250 ml of saturated aqueous solution of ammonium chloride and ice, the mixture is alkalinized with concentrated ammonium hydroxide and is extracted with ether. The ether solution is extracted with 10% hydrochloric acid; the resulting aqueous layer is heated at reflux temperature for one hour, and is then alkalinized with concentrated ammonium hydroxide and is extracted with ether. The resulting solution is dried with sodium sulfate. Once the solvent has evaporated, 35 g of an oil are obtained (37.7% yield) from which the picrate is precipitated. A sample thereof recrystallized from absolute ethanol presents a 165°–70° C. melting group.

Calculated analysis for $C_{18}H_{18}N_4SO_7$(I,R=H). C, 49.76; H, 4.14; N, 12.90; S, 7.37;

Found: C, 49.59; H, 4.31; N, 12.78; S, 7.66.

EXAMPLE 2

Obtaining 6,7,10-trimethyl-5,9-imino-4,5,8,9-tetrahydrocyclooct[b]-thiophene (I,R=CH₃)

Analogous to Example 1 starting from 1,3,4-trimethyl-pyridinium iodide. An analytic sample of the corresponding picrate is recrystallized from ethanol and presents a 200°–30° C. melting point.

Calculated analysis for $C_{19}H_{20}N_4SO_7$(I,R=CH₃). C=50.91; H=4.46; N=12.50; S=7.15;

Found: C=50.74; H=4.69; N=12.40; S=7.37.

PHARMACOLOGICAL PROPERTIES OF 7,10-DIMETHYL-5,9-IMINO-4,5,8,9-TETRAHYDRO-CYCLOOCT[b]THIOPHENE (R=H)

The product has analgesic activity. Its toxicity and activity has been compared with that of dextropropoxyphene.

A - ACUTE TOXICITY

Acute toxicity studies have been made in albino Swiss I.C.R. mice, of both sexes, of a weight of 30±2 g, kept without food for 24 hours prior to the experiment. Temperature and relative humidity of the atmosphere were kept constant. The products were administered intraperitoneally, the number of deaths having been noted 48 hours after treatment. The lethal dose ($LD_{50}$) was calculated by the Litchfield-Wilcoxen test. The following are the results obtained:

TABLE I

| Product | $LD_{50}$ (mg/kg) |
| --- | --- |
| I | 159.4 |
| Dextropropoxyphene | 140 |

B - ANALGESIC ACTIVITY

1. Thermal analgesia

The thermal analgesic effect has been studied in albino Swiss I.C.R. mice. The 55° C. hot-plate technique has been used. Batches of 10 mice were made.

The products under study were administered intraperitoneally. After 30 minutes the mice were placed on the hot-plate and note was made of the time it took them to jump, in seconds. Batches were made of control animals injected only with distilled water. The results are shown in Table II.

TABLE II

| Treatment | Dose | Jumping time in sec. $\bar{X} \pm$ S.E.M.(1) | Signif. of differences Control | Dextropropox |
|---|---|---|---|---|
| Control | — | 64 ± 7.911 | — | — |
| I | 50 mg/kg | 114.2 ± 11.168 | P<0.01 | P<0.01 |
| Dextropropoxyphene | 50 mg/kg | 164 ± 7.319 | P<0.00005 | — |

(1)Average values ± standard error of the mean Product I shows analgesic activity, but of less potency than that of dextropropoxyphene.

Product I shows analgesic activity, but of less potency than that of dextropropoxyphene.

2. Chemical analgesia

The analgesic effect has been studied in white Swiss I.C.R. mice, with the acetic acid writhing technique. Batches of 10 mice were made.

The products under study were administered intraperitoneally, and after 30 minutes 0.25 ml of 1% acetic acid were injected intraperitoneally. A batch of control animals received only the acetic acid. The number of writhes in each mouse were noted 20 minutes after the acetic acid was administered. The results are shown in Table III.

TABLE III

| Treatment | Dose | No. of writhes $\bar{X} \pm$ S.E.M | Signif. of differences Control | Dextropropox. |
|---|---|---|---|---|
| Control | — | 130 ± 7.764 | — | — |
| I | 25 mg/kg | 85.3 ± 13.915 | P<0.02 | N.S. |
| Dextropropoxyphene | 25 mg/kg | 68.4 ± 5.258 | P<0.00005 | — |

Product I shows the same analgesic activity as dextropropoxyphene.

What is claimed:

1. A process for obtaining 7,10-dimethyl-5,9-imino-4,5,8,9-tetrahydro-cyclooct[b]thiophenes of formula I:

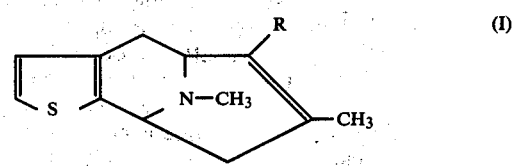

in which R is H (I,R=H) or a lower alkyl group, for example methyl (I,R=CH3), or the pharmacologically acceptable addition salts thereof, which comprises reacting 3-thienylmagnesium bromide obtained in conditions of high dilution and in inert atmosphere with a N-methyl-pyridinium iodide in anhydrous ether maintained at reflux temperature, with which an unstable dihydropyridine intermediate is obtained which without subsequent purification is treated in acid medium, leading to the formation of the corresponding 7,10-dimethyl-5,9-imino-4,5,8,9-tetrahydro-cyclooct[b]thiophene (I).

2. A compound selected from the group consisting of 7,10-dimethyl-5,9-imino-4,5,8,9-tetrahydro-cyclooct[b]-thiophene and 6,7,10-trimethyl-5,9-imino-4,5,8,9-tetrahydro-cyclooct[b]thiophene or their addition salts with pharmacologically acceptable acids.

3. An analgesic composition containing a compound of claim 2 in a pharmacologically effective amount along with a suitable inert carrier.

4. A compound of the formula:

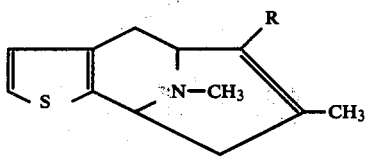

where R is H or lower alkyl or a pharmaceutically acceptable acid addition salt thereof.

5. An analgesic composition containing a compound of claim 4 in a pharmaceutically effective amount along with a suitable inert carrier.